(12) United States Patent
Cornacchia (10) Patent No.: US 9,433,460 B2
(45) Date of Patent: Sep. 6, 2016

(54) ELECTROSURGERY ACTUATOR

(71) Applicant: Bipad, LLC, Point Lookout, NY (US)

(72) Inventor: Louis Cornacchia, Point Lookout, NY (US)

(73) Assignee: BIPAD, LLC, Point Lookout, NY (US)

( * ) Notice: Subject to any disclaimer, the term of this patent is extended or adjusted under 35 U.S.C. 154(b) by 0 days.

(21) Appl. No.: 14/726,490

(22) Filed: May 30, 2015

(65) Prior Publication Data

US 2015/0342667 A1 Dec. 3, 2015

Related U.S. Application Data (60) Provisional application No. 62/005,290, filed on May 30, 2014.

(51) Int. Cl.
*A61B 18/12* (2006.01)
*A61B 18/14* (2006.01)
*A61B 18/00* (2006.01)

(52) U.S. Cl.
CPC ....... *A61B 18/1442* (2013.01); *A61B 18/1206* (2013.01); *A61B 2018/0094* (2013.01); *A61B 2018/00178* (2013.01); *A61B 2018/00589* (2013.01); *A61B 2018/00595* (2013.01); *A61B 2018/00601* (2013.01); *A61B 2018/00708* (2013.01); *A61B 2018/00922* (2013.01);
(Continued)

(58) Field of Classification Search
CPC .......... A61B 2018/00708; A61B 2018/00916; A61B 2018/00922; A61B 2018/00928; A61B 2018/00958; A61B 18/1206; A61B 18/1442; A61B 2018/00178; A61B 2018/00589; A61B 2018/00595; A61B 2018/00601; A61B 2018/0094; A61B 2018/1462
See application file for complete search history.

(56) References Cited

U.S. PATENT DOCUMENTS

| 4,552,143 A | 11/1985 | Lottick |
| 5,116,333 A | 5/1992 | Beane |
| 5,282,799 A * | 2/1994 | Rydell ............... A61B 18/1402 604/35 |

(Continued)

FOREIGN PATENT DOCUMENTS

| EP | 0834891 A2 | 4/1998 |
| EP | 1347705 B1 | 12/2005 |

(Continued)

OTHER PUBLICATIONS

International Search Report for PCT/US2015/033429 dated Aug. 25, 2015, 3 pp.

(Continued)

*Primary Examiner* — Jaymi Della
(74) *Attorney, Agent, or Firm* — David M. Quinlan, P.C.

(57) ABSTRACT

A system for selectively actuating a heating current conductible from a bipolar generator to a surgical tool may comprise an actuator assembly having an output receptacle, an input plug, and an actuating component. The output receptacle may be configured to receive a complementary tool plug of the surgical tool. The input plug may be configured for mating with a generator receptacle receivable of the heating current from the bipolar generator. The generator receptacle may be complementary to the tool plug. The actuating component may have at least one of a switch and a lever arm and may be configured to communicate with the bipolar generator for selectively actuating the heating current to flow from the input plug to the output receptacle upon engagement of the switch or the lever arm.

17 Claims, 10 Drawing Sheets

(52) U.S. Cl.
CPC ............... *A61B2018/00928* (2013.01); *A61B 2018/00958* (2013.01); *A61B 2018/1462* (2013.01)

(56) References Cited

U.S. PATENT DOCUMENTS

| | | | |
|---|---|---|---|
| 5,472,442 A * | 12/1995 | Klicek | A61B 18/1482 606/34 |
| 5,634,924 A | 6/1997 | Turkel et al. | |
| 5,860,975 A * | 1/1999 | Goble | A61B 18/1445 606/41 |
| 6,106,524 A * | 8/2000 | Eggers | A61B 5/0531 606/41 |
| 6,235,027 B1 | 5/2001 | Herzon | |
| 6,551,312 B2 | 4/2003 | Zhang et al. | |
| 6,569,163 B2 | 5/2003 | Hata et al. | |
| 6,747,218 B2 | 6/2004 | Huseman et al. | |
| 7,534,243 B1 | 5/2009 | Chin et al. | |
| 7,578,815 B2 | 8/2009 | Howell | |
| 7,695,470 B1 | 4/2010 | Stewart et al. | |
| 7,803,152 B2 * | 9/2010 | Honda | A61B 1/00039 200/86.5 |
| 8,075,559 B2 | 12/2011 | Stewart et al. | |
| 8,133,219 B2 | 3/2012 | Sato | |
| 8,317,784 B2 | 11/2012 | Choe et al. | |
| 8,479,969 B2 | 7/2013 | Shelton, IV | |
| 8,534,528 B2 | 9/2013 | Shelton, IV | |
| 8,558,880 B2 | 10/2013 | Nambakam et al. | |
| 8,568,400 B2 | 10/2013 | Gilbert | |
| 8,622,274 B2 | 1/2014 | Yates et al. | |
| 8,632,535 B2 | 1/2014 | Shelton, IV et al. | |
| 8,638,057 B2 | 1/2014 | Goldberg et al. | |
| 8,638,191 B2 | 1/2014 | Hamel et al. | |
| 8,652,120 B2 | 2/2014 | Giordano et al. | |
| 8,684,253 B2 | 4/2014 | Giordano et al. | |
| 8,747,400 B2 | 6/2014 | Bigley et al. | |
| 8,840,603 B2 | 9/2014 | Shelton, IV et al. | |
| 2002/0128646 A1 | 9/2002 | Zhang et al. | |
| 2004/0172011 A1 | 9/2004 | Wang et al. | |
| 2005/0267553 A1 | 12/2005 | Staunton et al. | |
| 2008/0140158 A1 | 6/2008 | Hamel et al. | |
| 2008/0319442 A1 | 12/2008 | Unger | |
| 2009/0085718 A1 | 4/2009 | Hamel et al. | |
| 2009/0248019 A1 | 10/2009 | Falkenstein et al. | |
| 2009/0275940 A1 * | 11/2009 | Malackowski | A61B 18/1442 606/42 |
| 2010/0087817 A1 | 4/2010 | Sato | |
| 2011/0077640 A1 * | 3/2011 | Rioux | A61B 18/1402 606/33 |
| 2011/0121049 A1 | 5/2011 | Malinouskas et al. | |
| 2011/0125138 A1 | 5/2011 | Malinouskas et al. | |
| 2011/0251612 A1 | 10/2011 | Faller et al. | |
| 2012/0116391 A1 | 5/2012 | Houser et al. | |
| 2012/0123405 A1 | 5/2012 | Moua et al. | |
| 2012/0172873 A1 | 7/2012 | Artale et al. | |
| 2013/0041292 A1 | 2/2013 | Cunningham | |
| 2014/0336634 A1 | 11/2014 | Gomez | |

FOREIGN PATENT DOCUMENTS

| | | |
|---|---|---|
| EP | 1596743 B1 | 4/2008 |
| EP | 2057955 A1 | 5/2009 |
| EP | 2324776 A2 | 5/2011 |
| EP | 2377476 A1 | 10/2011 |
| EP | 2377476 B1 | 3/2015 |
| WO | 2006/050410 A1 | 5/2006 |

OTHER PUBLICATIONS

Written Opinion for PCT/US2015/033429 dated Aug. 25, 2015, 8 pp.

* cited by examiner

ELECTROSURGERY ACTUATOR

CROSS-REFERENCE TO RELATED APPLICATIONS

The present application claims priority to U.S. Provisional Application No. 62/005,290 filed on May 30, 2014 and entitled BIPOLAR ELECTROCAUTERY ACTUATOR, the entire contents of Application 62/005,290 being expressly incorporated by reference herein.

BACKGROUND

Bipolar electrosurgery, including bipolar electrocautery, is widely used to apply a heating current to a very localized volume of tissues in order to achieve hemostasis (cauterization, coagulation) or to dissect (cut) tissues, such as during neurosurgery. Typically, a bipolar generator resting near the operating table generates steady or intermittent voltages which are delivered through a power cord to a bipolar electrosurgical tool, such as a forceps. A foot pedal controller operated by the surgeon connects to the bipolar generator through a pedal control line separate from the power cord delivering the heating current to the forceps. Unfortunately, the location of the pedal controller is often not aligned with the surgeon's foot, requiring that the surgeon grope for the pedal or contort his or her body position in order to depress the correct pedal, posing significant risk and delay to the surgery in progress.

One solution is to have a surgeon's assistant move the pedal controller to a position which is close to the surgeon's foot. But this, again, adds delay to the surgery. Further, if the surgeon moves to another standing position, the location of the pedal controller may no longer be reliably known by the surgeon. Additionally, the pedal control line is an additional cable in an operating room already full of instruments and cables, and may thereby create clutter and a risk of falling.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an embodiment, there is disclosed a system for selectively actuating a heating current conductible from a bipolar generator to a surgical tool and which may comprise an actuator assembly having an output receptacle, an input plug, and an actuating component. The output receptacle may be configured to receive a complementary tool plug of the surgical tool. The input plug may be configured for mating with a generator receptacle receivable of the heating current from the bipolar generator. The actuating component may have at least one of a switch and a lever arm and may be configured to communicate with the bipolar generator for selectively actuating the heating current to flow from the input plug to the output receptacle upon engagement of the switch or the lever arm.

In another embodiment, there is disclosed a system for selectively actuating a heating current conductible from a bipolar generator to a surgical tool, and which may comprise two elongated conducting members extending from a base end of the surgical tool to a heating end of the surgical tool. The base end may be configure to receive the heating current from the bipolar generator through a power cord. The heating end may effectuate at least one of the following modes of operation of the surgical tool: cutting, coagulation. An actuator assembly may interpose one of the power cord and at least one of the elongated conducting members within a base portion of the surgical tool nearer the base end. The interposing may result in a generator terminal conductive to the bipolar generator and a tip terminal conductive to the heating end. The actuator assembly may comprise an actuating component having at least one of a switch and a lever arm and being configured to communicate with the bipolar generator to selectively actuate the heating current to flow from the generator terminal to the tip terminal upon engagement of the switch or the lever arm.

In yet another embodiment, there is disclosed a method for selectively actuating a heating current conductible from a bipolar generator to an electrosurgical forceps, and which may comprise interposing an actuating component along an available current path extending between a handle of the forceps and the bipolar generator. The bipolar generator may be capable of delivering the heating current for effectuating at a heating end of the forceps at least one of a cutting mode and a coagulation mode. The method may further comprise disposing on the actuating component at least one of a switch and a lever arm. The method may further comprise engaging the switch or the lever arm by one of a surgeon and a surgeon's assistant, the switch or the lever arm being configured for human operation by one of a hand and an upper body. The method may further comprise the actuating component communicating with the bipolar generator to selectively actuate the heating current to flow to the heating end of the forceps upon engagement of the switch or the lever arm.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

When elements are referred to as being "connected" or "coupled," the elements can be directly connected or coupled together or one or more intervening elements may also be present. In contrast, when elements are referred to as being "directly connected" or "directly coupled," there are no intervening elements present.

Figure 1:
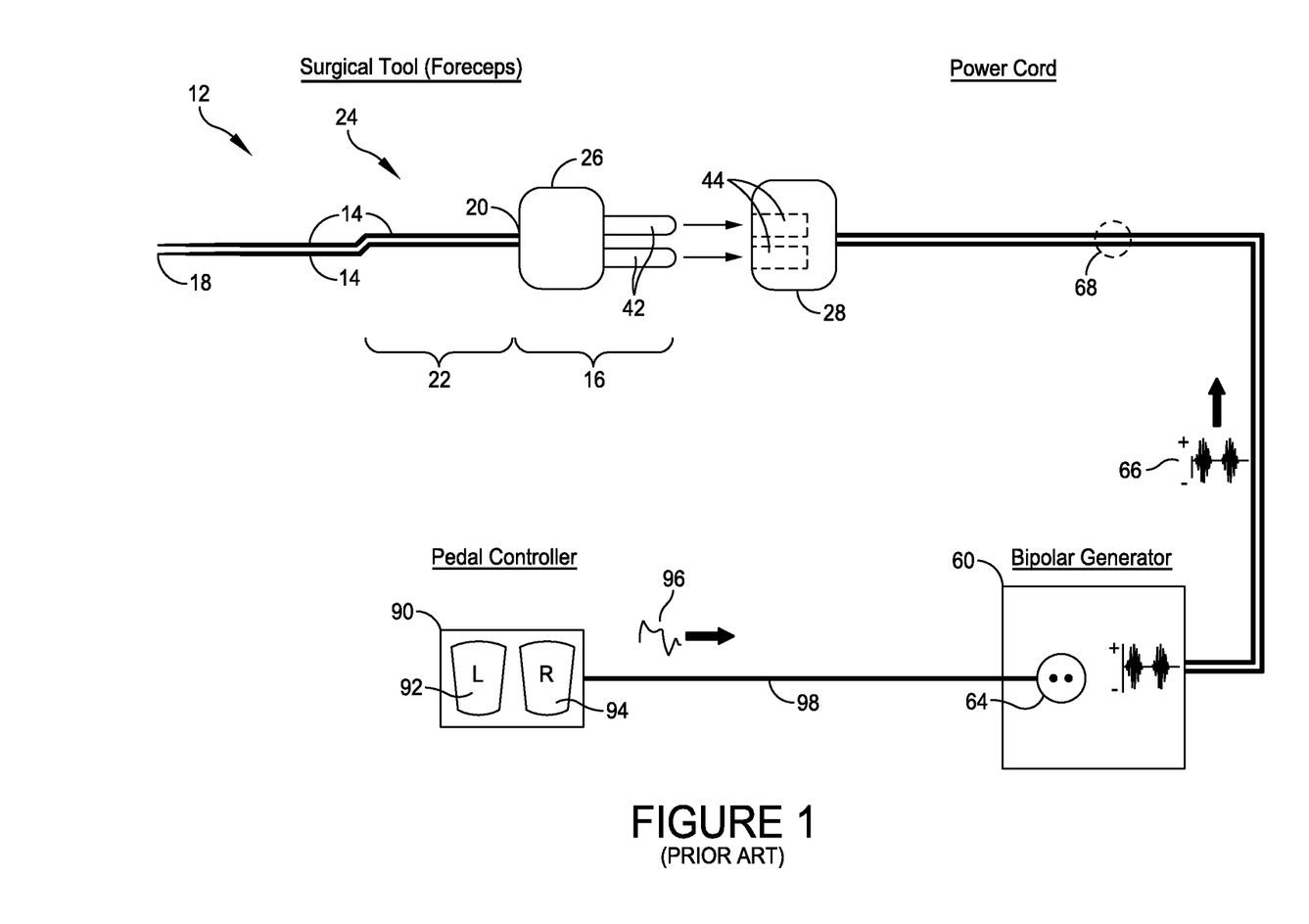
FIG. 1 (prior art) illustrates an embodiment of foot pedals used to initiate the flow of a heating current to electrosurgical forceps.
Figure 2A:
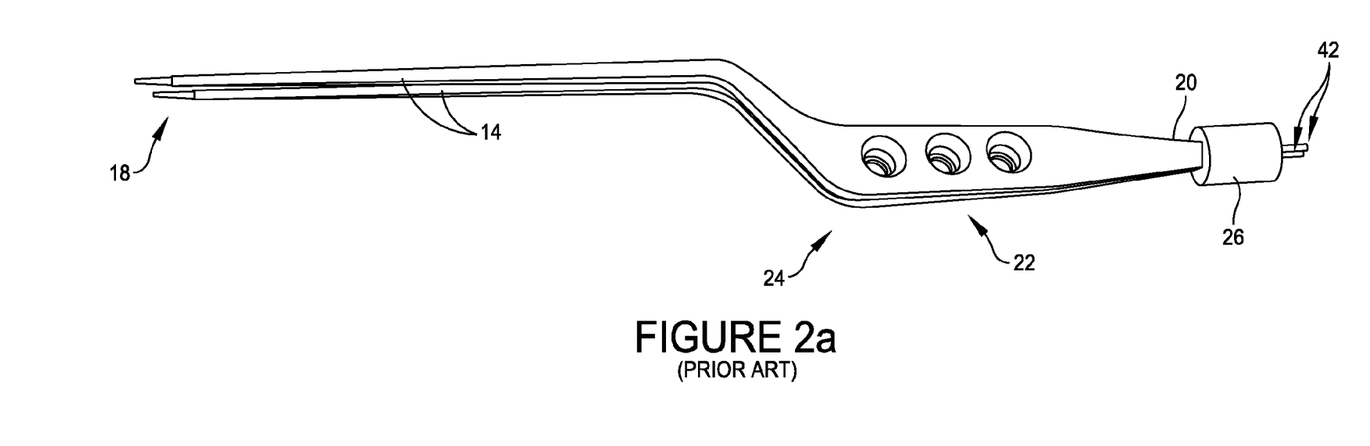
FIGS. 2a-2b (prior art) illustrates an embodiment of electrosurgical forceps connected by a tool plug.
Figure 2B:
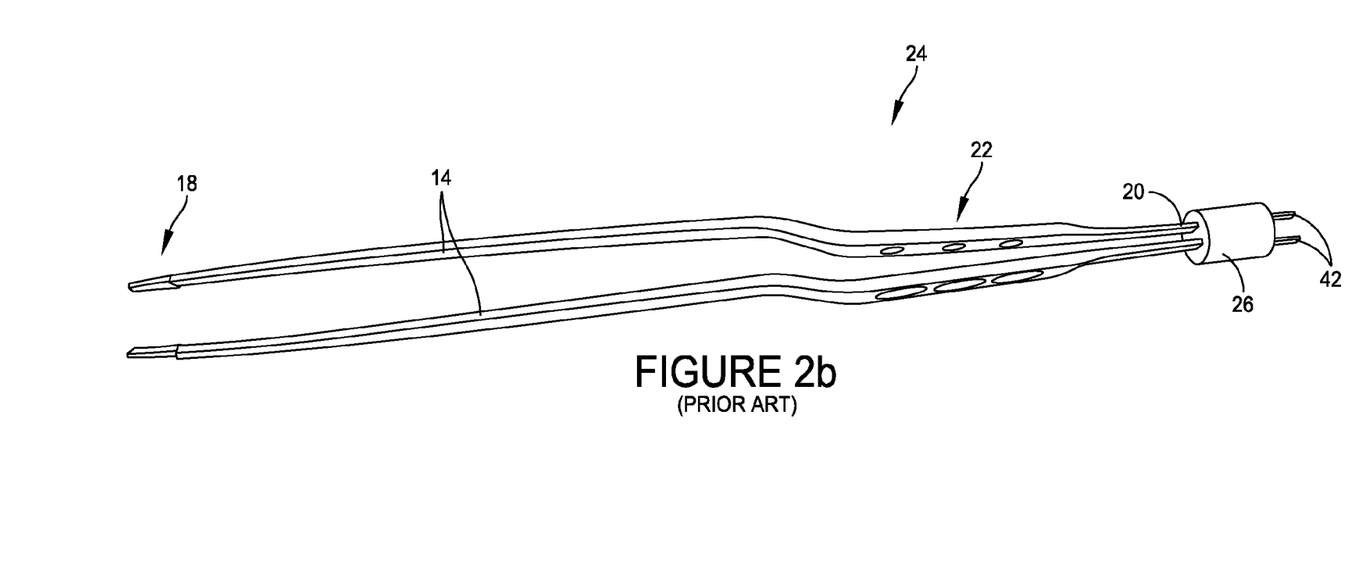

FIGS. 1 and 2a-2b illustrate a prior art system where pedal controller 90 may actuate bipolar generator 60 by means of pedal signaling 96 directed along pedal control line 98 and into control input 64. Left pedal 92 may be depressed to actuate a cutting mode for forceps 12, while right pedal 94 may be depressed to actuate a coagulation mode. In response to signals on pedal control line 98, a heating current 66 may be dispatched from bipolar generator 60 onto power cord 68 which may terminate in generator receptacle 28 having sockets 44. A power connector (not shown) on bipolar generator 60 may output the heating current 66 into a removably connectable power cord 68. The voltage waveform of heating current 66 may be intermittent for coagulation mode, as shown in FIG. 1, or may be continuous for cutting mode. Surgical tool (forceps) 12 may receive the heating current 66 through prongs 42 of tool plug 16 plugged into generator receptacle 28.

Continuing with FIGS. 1 and 2a-2b, two elongated blades 14 may be coated with an insulator or various insulation materials on all parts extending from base end 20 to heating end 18 in order to avoid a short circuit. However, the blades may be bare on the inside tips near heating end 18 for grabbing tissues to be cauterized or dissected by the passage of heating current 66. Heating current 66 may be an alternating current and have a frequency ranging from approximately 200 kHz to approximately 4.0 MHz. A handle 22 may be held by a surgeon and may allow for articulation of blades 14. Blades 14 may be insulatively bound together by insulator 26 and may allow for articulation of blades 14. Insulator 26 may also retain prongs 42 of tool plug 16. Base portion 24 may refer to the portion of the tool 12 closest to tool plug 26 and which is not involved in surgical effect, and may be approximately concurrent with handle 22.

Figures 3A, 3B:
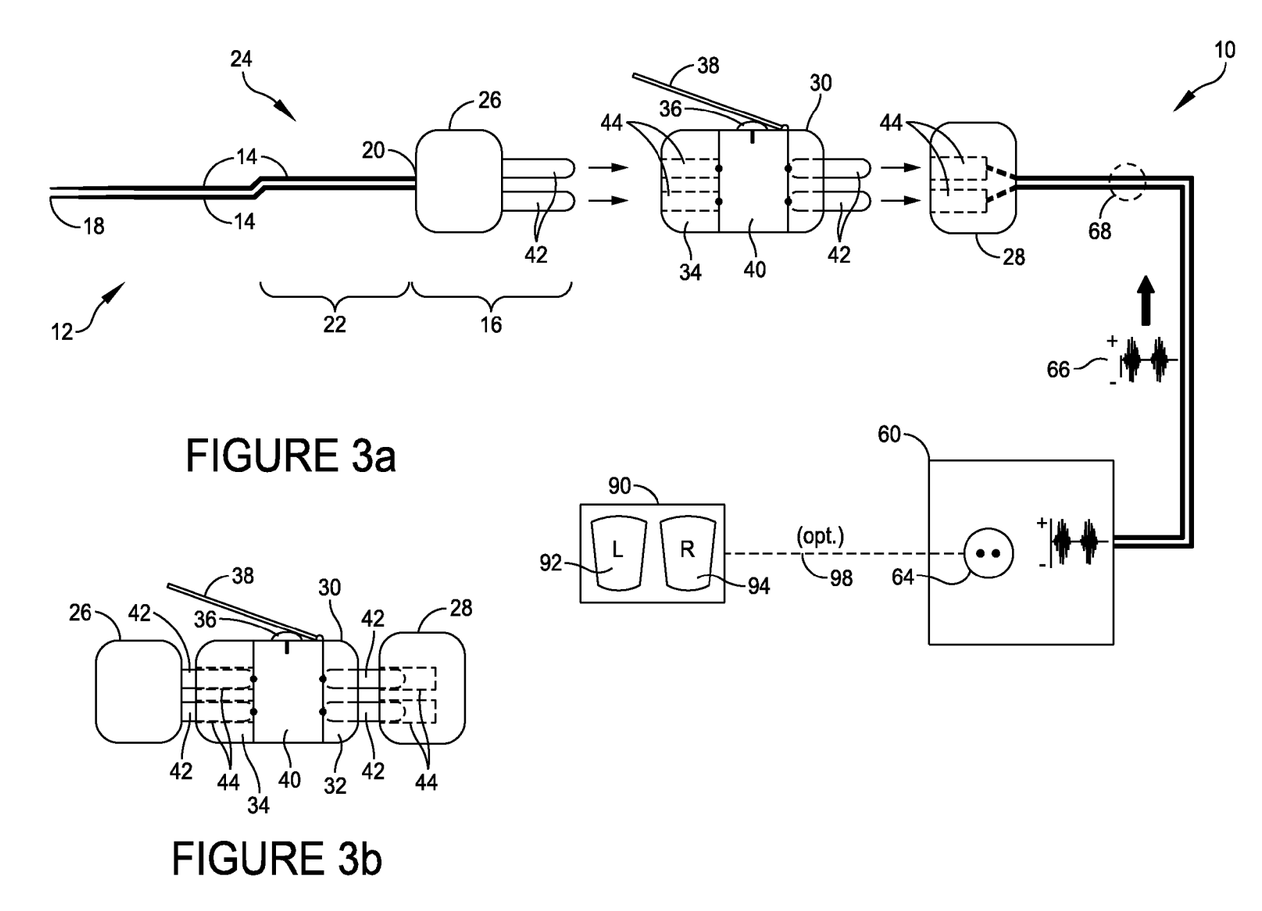
FIGS. 3a-3b illustrate an exemplary embodiment of an in-line actuator assembly for a bipolar electrosurgical actuating system and method, in accordance with an embodiment of the present disclosure.

Now referring to FIGS. 3a-3b, 4a-4b, 5a-5b, and 6-8, in various embodiments, a bipolar electrosurgical actuating system 10 may comprise an actuator assembly 30 having an output receptacle 34 with sockets 44, an input plug 32 with prongs 42, and an actuating component 40 arranged to pass a heating current 66 from prongs 42 to sockets 44. Actuator assembly 30 may be interposed in-line between a tool plug 16 of surgical tool (forceps) 12 and a generator receptacle 28 complementary to tool plug 16, as shown in FIG. 3b. The connector type chosen for output receptacle 34 and input plug 32 may be selected to match the size, style, and gender of the connector used by surgical tools 12 of different manufacture. Actuating component 40 may include a switch 36 and a lever arm 38 and may be configured to communicate with bipolar generator 60 for selectively actuating the heating current 66 to flow from input plug 32 to output receptacle 34 upon engagement of the switch 36 or the lever arm 38. Alternately, actuating component 40 may include only a switch 36 or only a lever arm 38. Various means known in the art may facilitate selective actuation of bipolar generator 60 and which are described below for FIGS. 6-8.

Continuing, in various embodiments, heating current 66 may pass through power cord 68 to generator receptacle 28, through actuator assembly 30, and into forceps 12 at tool plug 16. Heating current 66 may then conduct through insulator 26 to base end 20 of blades 14 for effectuating at least one of a cutting mode and a coagulation mode at heating end 18. Base portion 24 may refer to the portion of the forceps 12 closest to tool plug 16 and which is not involved in surgical effect, and may be approximately concurrent with handle 22. Generalizing, surgical tool 12 may include two elongated conducting members (blades 14) terminating in a heating end 18. Alternatives to a forceps may include a hemostat, a scissors, a clamp, a clip, a scalpel, a hook, and a loop. Alternatives to the prong 42 and socket 44 connectors may include a wire terminal, a bayonet twist mount, a flush mount with screws, locking pins with a release, a snap, and a clamp. Alternatively, the tool plug 16 and input plug 32 may be configured as female connectors and the generator receptacle and output receptacle may be configured as male connectors. In another embodiment, not shown, assembly 30 may include a jumper cord (not shown) interposed between actuating component 40 and input plug 32, where generator receptacle 28 may be a power connector (not shown) mounted on the bipolar generator and outputting heating current 66 into an actuator assembly that includes the power cord feature. In this case, input plug 32 is chosen to mate with the power connector at bipolar generator 60.

Figure 4A:
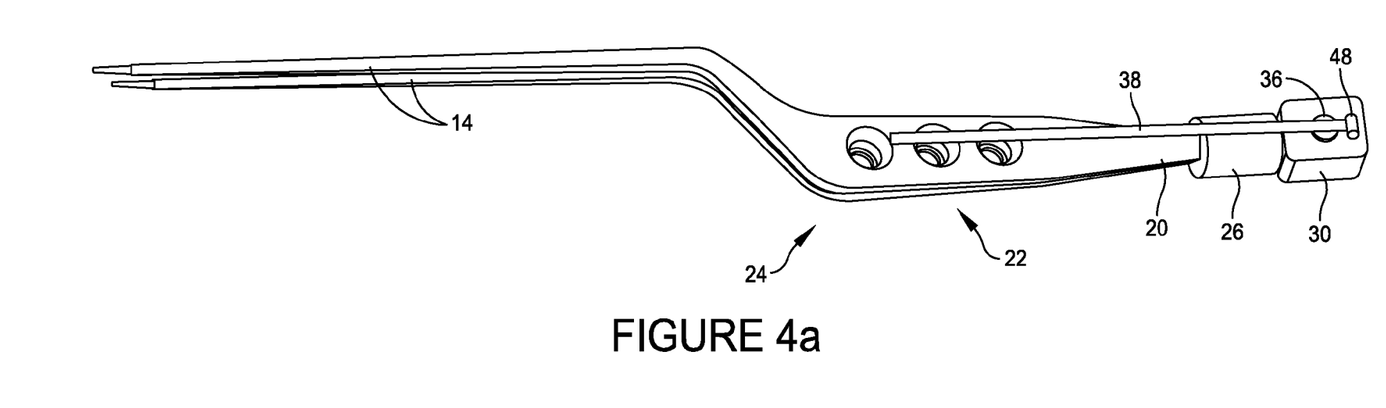
FIGS. 4a-4b illustrate an exemplary embodiment of an actuator assembly mounted to a forceps for a bipolar electrosurgical actuating system and method.
Figure 4B:
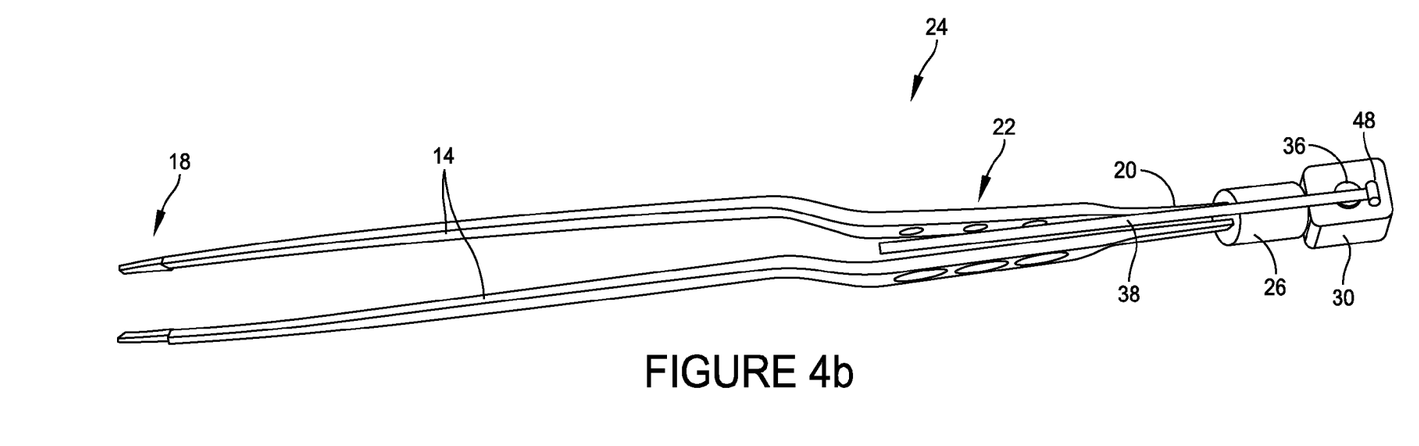
Figures 5A, 5B:
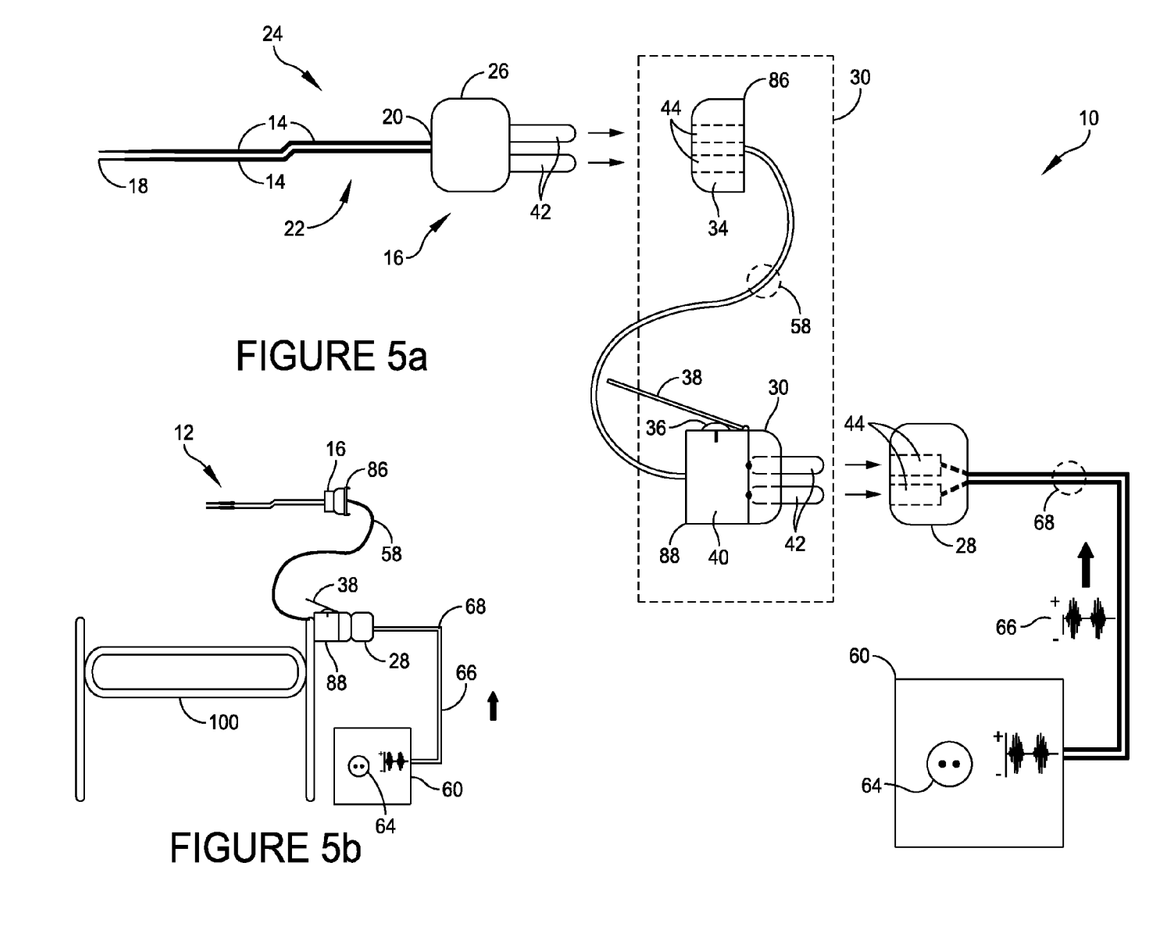
FIGS. 5a-5b illustrate an exemplary embodiment of an in-line actuator assembly separated by a jumper cord for a bipolar electrosurgical actuating system and method.
Figure 6:
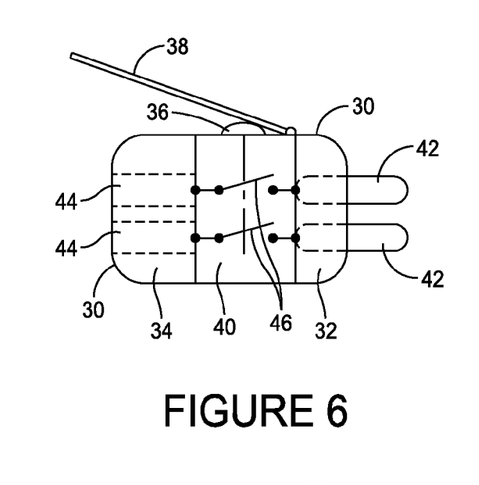
FIG. 6 illustrates an exemplary embodiment of a hard electrical switch for facilitating an actuating component for a bipolar electrosurgical actuating system and method.
Figure 7:
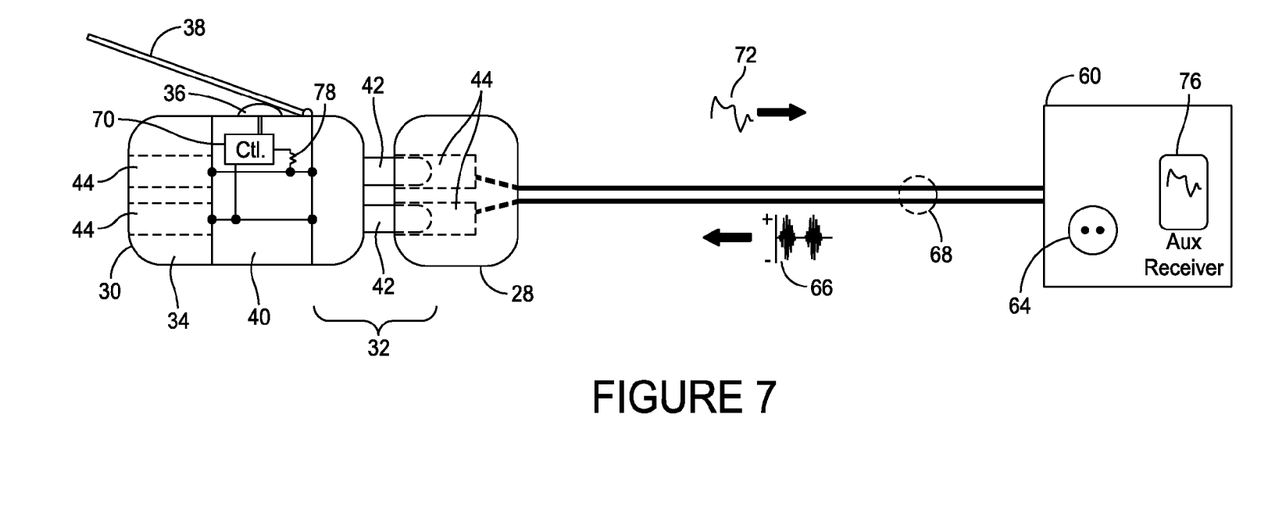
FIG. 7 illustrates an exemplary embodiment of a control signaling component coupled to the input plug for facilitating an actuating component for a bipolar electrosurgical actuating system and method.
Figure 8:
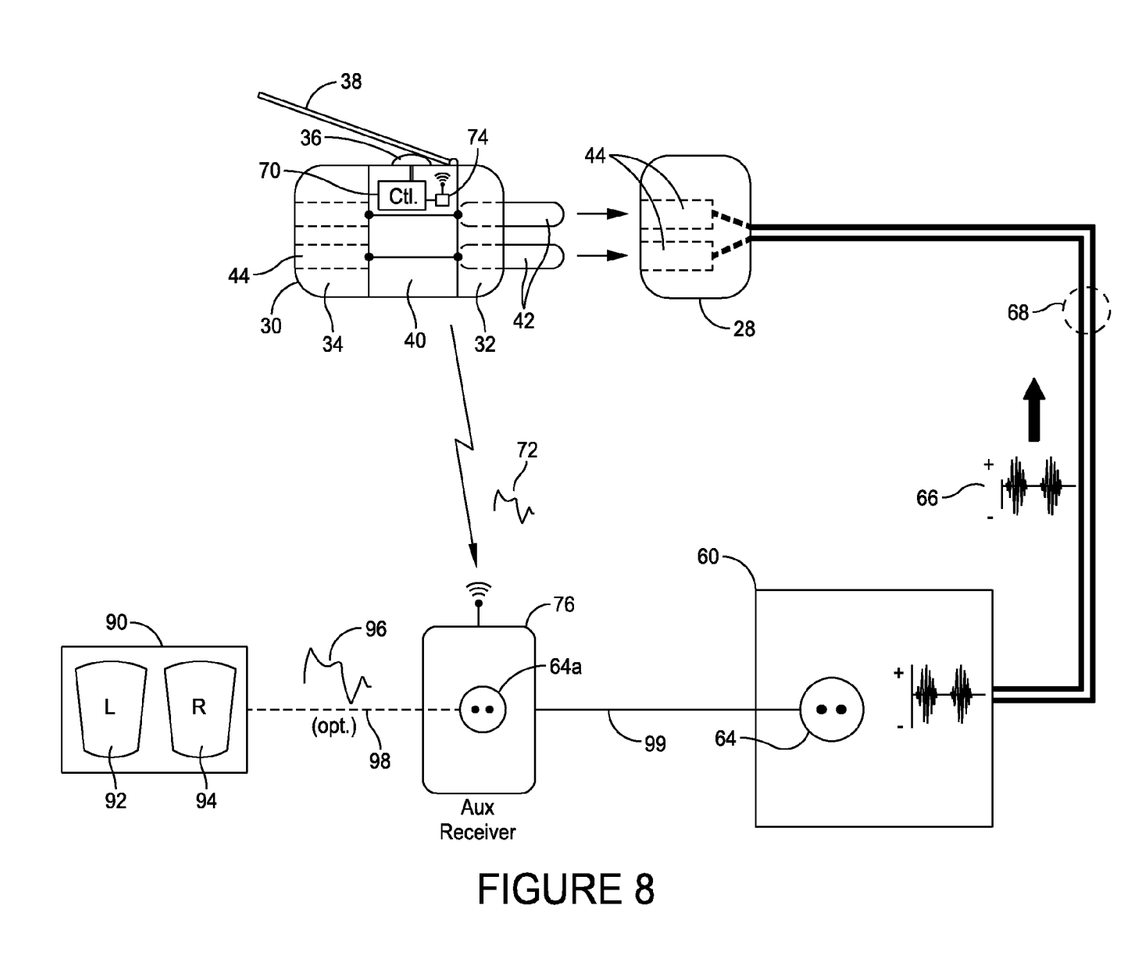
FIG. 8 illustrates an exemplary embodiment of a control signaling transmitted to an auxiliary receiver for facilitating an actuating component for a bipolar electrosurgical actuating system and method.

Referring still to FIGS. 3a-3b, 4a-4b, 5a-5b, and 6-8, in various embodiments, pedal controller 90 may optionally be connected to bipolar generator 60 by pedal control line 98 for offering an additional method of selectively actuating bipolar generator 60. Left pedal 92 and right pedal 94 may be depressed to actuate a cutting mode or a coagulation mode, respectively. In an embodiment, selective actuation of bipolar generator 60 may be accomplished by a hard electrical switch 46 included in actuating component 40 and engaged by switch 36 for directly conducting the heating current 66 from input plug 32 to output receptacle 34 (FIG. 6). In another embodiment, selective actuation of bipolar generator 60 may be accomplished by a control circuit 70 included in actuating component 40 and generating a control signaling 72 conductively or inductively coupled by signaling tap 78 to input plug 32 for communicating with bipolar generator 60 for selectively actuating heating current 66 (FIG. 7). In yet another embodiment, selective actuation of bipolar generator 60 may be accomplished by an actuator transmitter 74 included in the actuating component 40, where a control signaling 72 may be wirelessly transmitted to and receivable by the bipolar generator 60 via auxiliary receiver 76 (FIG. 8). Additional description for FIGS. 6-8 is provided below.

Continuing with FIGS. 3a-3b, 4a-4b, 5a-5b, and 6-8, in various embodiments, lever arm 38 may be hingedly moveable to engage switch 36 for selectively actuating the heating current 66. For example, lever arm 38 may be hinged at one end and configured to depress a momentary push button switch 36 when lever arm 38 is moved downward and toward assembly 30. Alternately, lever arm 38 may engage a rocker switch 36 (not shown) during a sideways movement parallel to the surface of assembly 30 and thereby actuate heating current 66. Referring to FIGS. 4a-4b, in an embodiment, lever arm 38 may extend over handle 22 along the sides of forceps 12 or the top or bottom of forceps 12, providing a convenient means for actuating heating current 66 using the same or opposite hand as the hand holding forceps 12. Lever arm 38 may be configured for operation by a human hand such that it conforms to the shape of the hand and its available range of motion to allow for a subtle and fault-free engagement without interfering with the articulation of forceps 12.

Still with FIGS. 3a-3b, 4a-4b, 5a-5b, and 6-8, in various embodiments, lever arm 38 may include a lever switch mechanism (not shown) for selectively actuating the heating current 66 in response to a displacement of the lever arm 38 by at least one of the following means: mechanical actuation, electrical resistance, piezoelectric pressure, electrostatic sensing. The displacement may be an angular pivoting, a pistoning of the lever shaft, a rotation the shaft, a flexing, or some other movement. The lever switch mechanism may eliminate a need for switch 36, or may provide additional control features in addition to those provided by switch 36. For example, lever arm 38 may be a rod extending from a piezoelectric 'joystick' base (lever switch mechanism). Switch 36 may be configured as at least one of a push button, a slide switch, a rotating shaft, a joystick, an electrostatic sensor, a piezoelectric sensor, a temperature switch, a rocker switch, a momentary switch, and a voice-activated switch. Switch 36 may be used alone or in combination with lever arm 38. Advantageously, having a flexible means for interposing a switch 36 and/or lever arm 38 in-line with power cord 68 may provide a visible and/or reliably known location for selectively actuating heating current 66.

Referring now to FIGS. 5a-5b, in an embodiment, a jumper cord 58 may connect a tool portion 86 of actuator assembly 30 to a generator portion 88 of actuator assembly 30, the tool portion 86 containing output receptacle 34 and connecting to tool plug 16, the generator portion 88 containing input plug 32 and actuating component 40 and connecting to generator receptacle 28. In various embodiments, jumper cord 58 may separate and provide conduction between input plug 32 and output receptacle 34 for mounting the actuating component 40 to an operating table 100. For example, lever arm 38, when positioned at operating table 100, may be engaged by a human hand or hip. Alternatively, jumper cord 58 may enable the actuating component 40 to be held by a human hand, held actuatably in a human mouth, mounted to a positioning arm, mounted actuatably to a human upper body, or mounted to another piece of operating room equipment. In other embodiments, actuating component 40 may be interposed anywhere along an available current path (FIG. 10) concurrent with power cord 68 and extending from handle 22 of a surgical tool 12 to bipolar generator 60. For example, in an embodiment not shown, assembly 30 may include jumper cord 58 for separating and providing conduction between actuating component 40 and input plug 32, where generator receptacle 28 may be a power connector (not shown) mounted on the bipolar generator and outputting heating current 66 into an actuator assembly that includes the power cord feature. In this case, generator receptacle 28 may not be complementary to tool plug 16. Advantageously, providing an in-line method for selectively actuating heating current 66 may allow actuating component 40 to be flexibly positioned for reliable access by some part of a human upper body, thereby removing the limitations and uncertainty of a pedal controller 90.

Referring now to FIG. 6, in various embodiments, selective actuation of bipolar generator 60 may be accomplished by hard electrical switches 46 closing a circuit between input plug 32 and output receptacle 34 for each respective conductor. Hard electrical switch 46 may be a single-pole-single-throw type that may be mechanically or electrically engaged by switch 36. Alternatively, one hard electrical switch 46 may close the circuit of one of two bipolar conducting paths, the other circuit being continually closed. In an embodiment, a heating current 66 may be available at generator receptacle 28 at a desired preset condition, and engagement of hard electrical switch 46 may close the circuit actuating bipolar generator 60 to conduct heating current 66 to surgical tool 12. In this case, the engagement of hard electrical switch 46 may constitute a communication with and an actuation of bipolar generator 60. For example, a surgeon may depress left pedal 92 for effectuating a cutting mode, and then engage switch 36 to pass the heating current 66 to a forceps 12 at the precise moment required. Advantageously, a precision cut may be engaged by a switch 36 or lever arm 38 located at or above a waist level and having a finer movement than a large, heavy foot pedal not visible to the surgeon.

Continuing with FIG. 6, in an embodiment not shown, selective actuation of bipolar generator 60 may be accomplished by a hard electrical switch closing a circuit between two auxiliary wires (not shown) incorporated into power cord 68 for tripping a relay (not shown) actuating the heating current 66. The relay may be internal to generator 60 or may be included in an auxiliary receiver that generates a pedal signaling 96 for control input 64. A continuous pass-through connection may exist between input plug 32 and output receptacle 34.

Referring to FIG. 7, in an embodiment, selective actuation of bipolar generator 60 may be accomplished by a control circuit 70 included in actuating component 40 and generating a control signaling 72 corresponding to an engagement of switch 36 or lever arm 38 and conductively or inductively coupled by signaling tap 78 to input plug 32 for communicating with bipolar generator 60 to selectively actuate heating current 66. Bipolar generator 60 may include auxiliary receiver 76 (which is illustrated internal to bipolar generator 60) for decoding control signaling 72. Receiver 76 may decode control signaling 72 into a control format similar to that of pedal signaling 96 conventionally received by pedal controller 90 for effectuating one of a cutting mode or a coagulation mode. Additionally, control signaling may effectuate an OFF mode where there is no current flow. A closed circuit may exist between receptacle 34 and input plug 32. Alternatively, in an embodiment not shown, auxiliary receiver 76 may be external to bipolar generator 60 and may collect a sample of control signaling 72 from a coupler or inductive strap (not shown) wrapped around power cord 68. Auxiliary receiver 76 may decode the control signaling 72 and may then direct the decoded output (not shown) into control input 64, thereby avoiding modifications to bipolar generator 60. Optionally, pedal controller 90 (FIGS. 3a and 8) may be plugged into an available control input 64 through pedal control line 98 for providing an additional means for actuating heating current 66.

Referring to FIG. 8, in an embodiment, selective actuation of bipolar generator 60 may be accomplished by an actuator transmitter 74 included in actuating component 40, where a control signaling 72 from control circuit 70 and corresponding to an engagement of switch 36 or lever arm 38 may be wirelessly transmitted to auxiliary receiver 76 external to bipolar generator 60. Auxiliary receiver 76 may then decode control signaling 72 into a suitable format (not shown) for communicating over auxiliary control line 99 into bipolar generator 60 at control input 64. Bipolar generator 60 may then effectuate a desired operational mode of surgical tool 12 based on the decoded output of auxiliary receiver 76. A closed circuit may exist between receptacle 34 and input plug 32. Alternatively, in an embodiment not shown, auxiliary receiver 76 may be internal to bipolar generator 60 for decoding control signaling 72 received wirelessly from actuator transmitter 74. Optionally, pedal controller 90 may be configured to secondarily actuate a cut mode or coagulation mode through pedal control line 98 routed into auxiliary receiver 76 (which is illustrated external to bipolar generator 60) at control input 64a. In an embodiment, auxiliary receiver 76 may combine pedal signaling 96 and control signaling 72 for selectively actuating bipolar generator 60 via auxiliary control line 99.

Referring to FIGS. 7-8, in various embodiments, control signaling 72 may incorporate additional control beyond those effectuating modes of electrosurgery. For example, control signaling may be configured for setting the voltage or duty cycle (not shown) of bipolar generator 60, and may also be configured for setting the operating conditions of other equipment in the operating room (not shown), such as by auxiliary receiver 76 receiving and routing commands directed to equipment other than bipolar generator 60. In other embodiments, actuator assembly 30 may include a microphone and a voice-activated switch for selectively actuating heating current 66.

Figure 9:
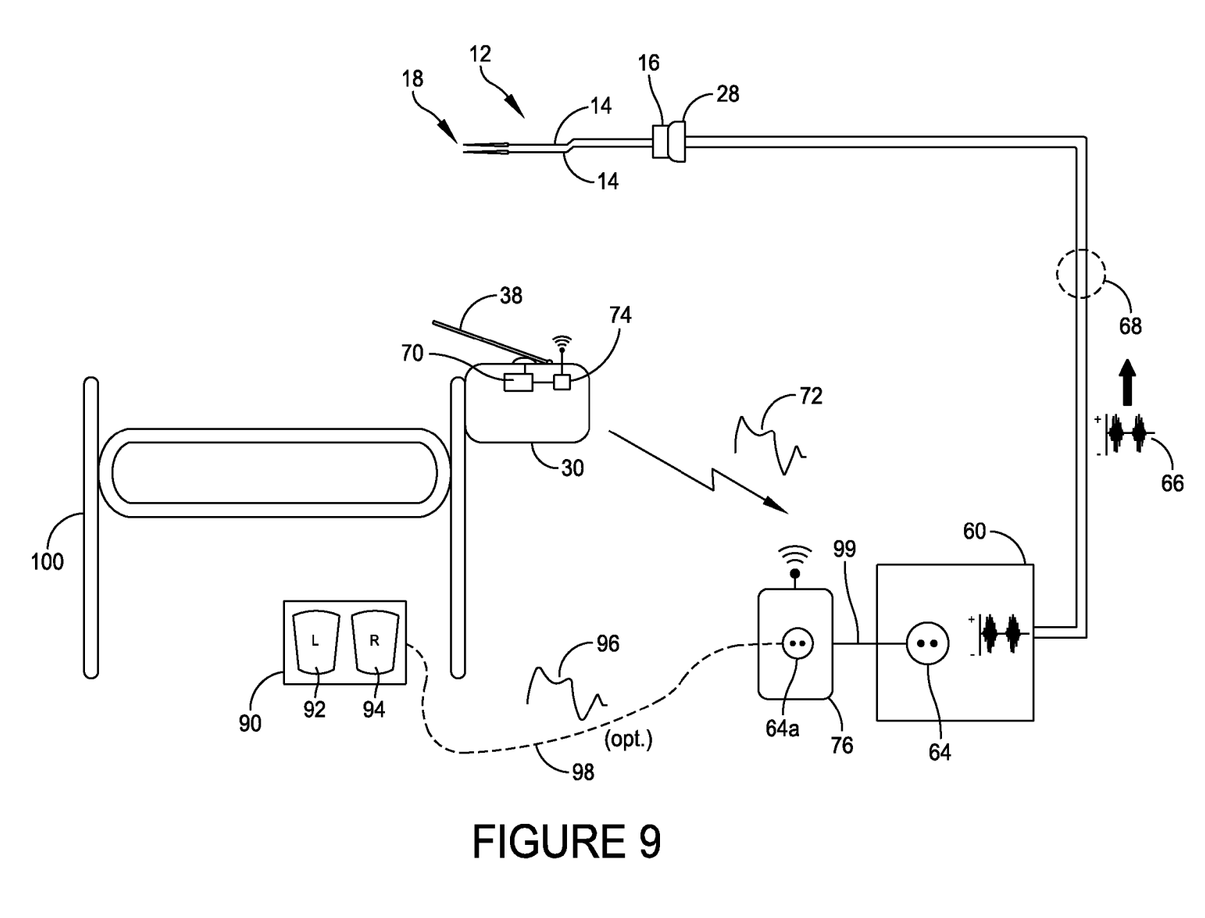
FIG. 9 illustrates an exemplary embodiment of using the actuator assembly as a remote control for a bipolar electrosurgical actuating system and method.

Referring to FIG. 9, in various embodiments, actuator assembly 30 may include a battery (not shown) for powering control circuit 70 and actuator transmitter 74, the actuator assembly 30 being removed from interposition between tool plug 16 and generator receptacle 28 in order to operate as a remote control and configured for mounting to operating table 100. In an embodiment, upon engagement of lever arm 38, control circuit 70 generates control signaling 72 which is received and decoded by auxiliary receiver 76, selectively actuating bipolar generator 60 through auxiliary control line 99 and control input 64. Upon actuation of bipolar generator 60, heating current 66 is conducted through power cord 68, through the connector pair composed of generator receptacle 28 and tool plug 16, and to the heating end 18 of blades 14 of forceps 12. In an embodiment, pedals 92 and 94 of pedal controller 90 may be depressed to send pedal signaling 96 over pedal control line 98 and into control input 64a for actuating bipolar generator 60.

Figure 10:
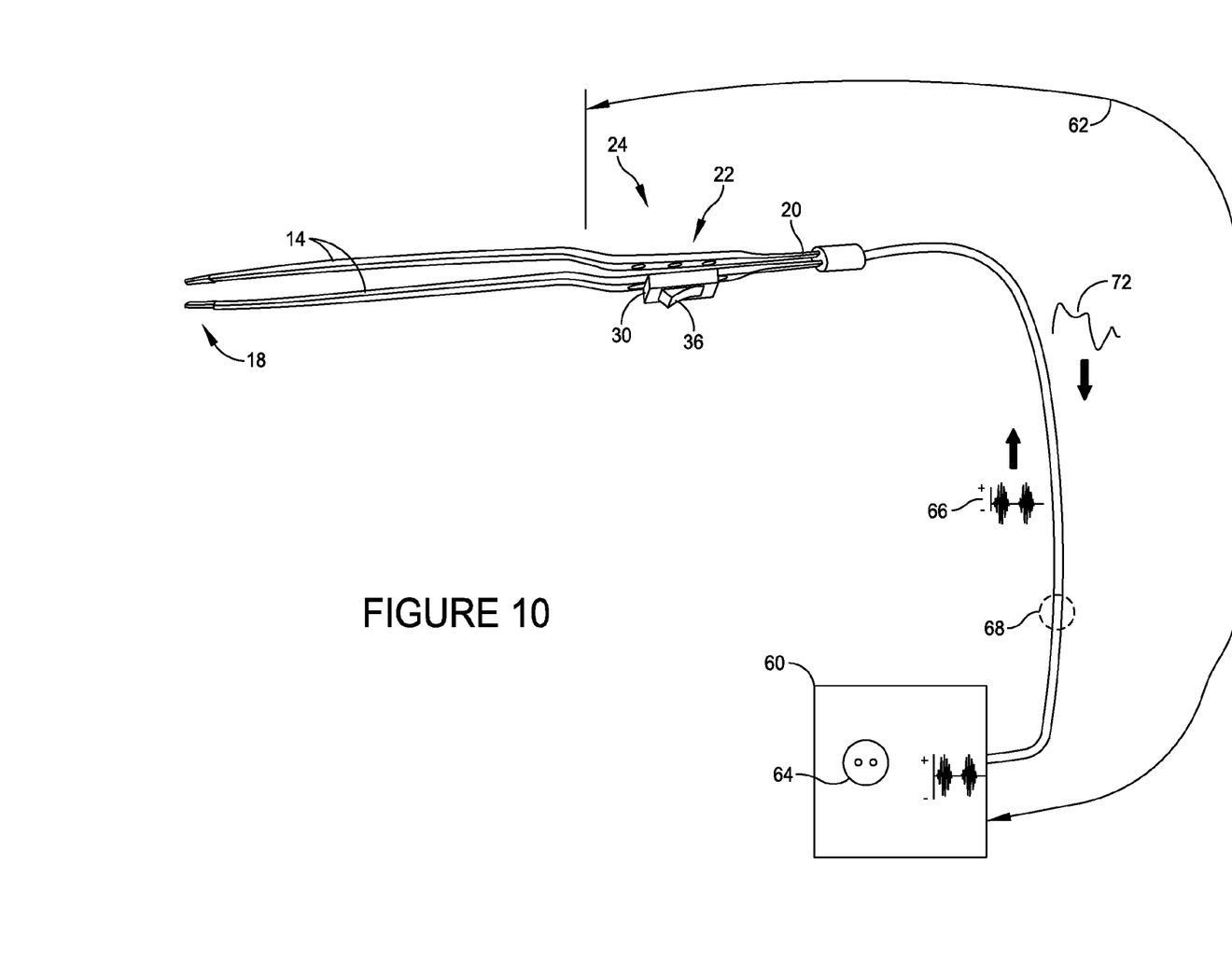
FIG. 10 illustrates an exemplary embodiment of an actuator assembly integrated into a forceps for a bipolar electrosurgical actuating system and method.

Continuing with FIGS. 9 and 10, in various embodiments, remote assembly 30 may be handheld, held actuatably in a human mouth, hingedly mounted to a shoe, mounted actuatably to a human upper body, mounted to a positioning arm, and mounted to at least one blade 14 of forceps 12. In an embodiment, actuator assembly 30 may include a blade coupling element (not shown) similar to signaling tap 78 for coupling control signaling 72 of a remote control assembly 30 onto one or both blades 14 of forceps 12. In various embodiments, the actuating component 40 (not shown) may be disposed with a switch (not shown), a lever arm 38, a lever switch mechanism 49 (not shown) integrated into lever arm 38, or a lever arm 38 and switch 36, each permutation for effectuating an electrosurgical mode, such as coagulation. Input plug 32 and output receptacle 34 (not shown) may be excluded from a remote control assembly or their contacts may be insulated.

Figure 11:
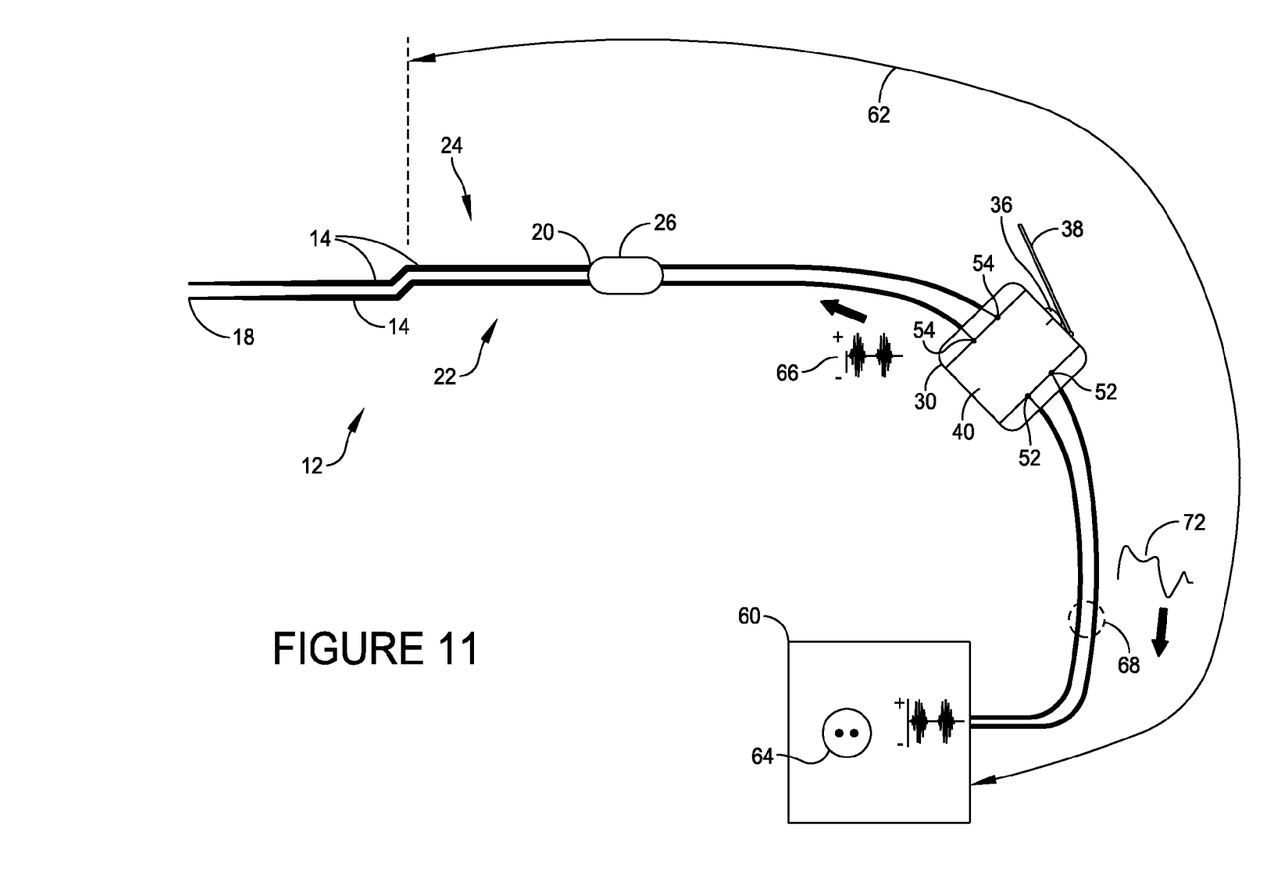
FIG. 11 illustrates an exemplary embodiment of an actuator assembly integrated into a power cord for a bipolar electrosurgical actuating system and method.

Referring now to FIGS. 10 and 11, in various embodiments, two elongated conducting members 14 extending from a base end 20 of surgical tool 12 to a heating end 18 may be configured to receive heating current 66 from the bipolar generator 60 through a power cord 68. The bipolar electrosurgical actuating system may include the actuating component of the actuator assembly in an integral configuration with the elongated conducting members. This integral configuration may be built into the base or blades of a bipolar forceps, which may be disposable or reusable or otherwise configured for single use or multiple uses.

There may be no connector intervening between power cord 68 and tool 12. An actuator assembly 30 may be interposed along an available current path 62 extending between a handle 22 of surgical tool 12 and bipolar generator 60, the interposing resulting in, for each conductor interposed, a generator terminal 52 (FIG. 11) conductive to bipolar generator 60 and a tip terminal 54 (FIG. 11) conductive to heating end 18. Actuator assembly 30 may include actuating component 40 having at least one of a switch 36 and a lever arm 38 and being configured to communicate with the bipolar generator 60 to selectively actuate heating current 66 to flow from generator terminal 54 to tip terminal 54 upon engagement of the switch 36 or the lever arm 38, as described for FIGS. 6-8 above. The flow of heating current 66 may be facilitated by at least one of the following actuating steps: closing a hard electrical switch 46 in actuating component 40 (FIG. 6), coupling a control signaling 72 from actuating component 40 onto the available current path 62 and receivable by bipolar generator 60 (FIGS. 7, 10-11), and wirelessly transmitting control signaling 72 from actuating component 40 to and receivable by bipolar generator 60 (FIG. 8).

Continuing with FIGS. 10 and 11, in various embodiments, actuator assembly 30 may be interposed in at least one of the elongated conducting members 14 within a base portion 24 of surgical tool 12 nearer base end 20 (FIG. 10). In an embodiment, switch 36 may comprise a rocker switch for permanent or momentary engagement of an operational mode, such as cauterization (FIG. 10). In embodiments not shown, actuating component 40 may include lever arm 38 extending over the forceps handle 22, as described for FIGS. 3a-3b and 4a-4b above. In another embodiment, actuator assembly 30 may be interposed in power cord 68, and may couple a control signaling 72 from actuating component 40 onto the power cord 68 for receiving by bipolar generator 60 (FIG. 11). Control input 64 may be optionally utilized a by pedal controller 90 (FIG. 3a) for actuating a heating current 66, or may be utilized by auxiliary receiver 76 (which is illustrated external to bipolar generator 60) (FIGS. 8 and 9) for conducting decoded control signaling 72 into bipolar generator 60, thereby selecting an operational mode such as coagulation, cutting, or an off mode.

Referring still to FIGS. 10 and 11, an in embodiment not shown, actuator assembly 30 may interpose power cord 68 where an input plug 32 is added to generator terminal 52 for mating to the power cord and where a blade connector (not shown) is added to tool terminal 54 for clipping or sliding onto forceps blades 14. In this embodiment, tool plug 16 may be bypassed or used strictly for mechanically mounting assembly 30, while heating current 66 may be routed through assembly 30 via the blade connector to blades 14 upon engagement of the switch 36 or the lever arm 38. In another embodiment, assembly 30 may include a jumper cord (functioning as power cord 68) between actuating component 40 and input plug 32, the assembly plugging into a power connector (not shown) mounted on bipolar generator 60 and outputting heating current 66 for delivery to blades 14 via the blade connector described above. In an embodiment, selective actuation may be accomplished by a hard electrical switch closing a circuit between two auxiliary wires (not shown) accompanying the two wires carrying heating current 66, the switch closing for tripping a relay (not shown) actuating the heating current. The relay may be internal to generator 60 or may be included in an auxiliary receiver that generates a pedal signaling 96 for control input 64.

Referring to FIGS. 9 and 10, in various embodiments, insulator 26 may insulatively bind conducting members 14 together, and may allow for their articulation by a surgeon. Additionally, insulator 26 may join power cord 68 with conducting members 14 without the use of connectors. In an embodiment, in FIG. 10, assembly 30 may be interposed on only one conducting member 14 and may acquire access to the second conductor of power cord 68 via a wire (not shown) channeled through member 14 from insulator 26, thereby completing a circuit for sending control signaling 72.

The foregoing description of the subject matter has been presented for purposes of illustration and description. It is not intended to be exhaustive or to limit the subject matter to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments except insofar as limited by the prior art.

What is claimed is:

1. A system for selectively actuating a heating current conductible from a generator to forceps, comprising:
    an actuator assembly having a tool portion containing an output receptacle, and a generator portion containing an input plug and an actuating component, the actuator assembly further comprising a longitudinal axis defined by a line extending, when the forceps are connected to the output receptacle, from a proximal end of the forceps to a distal end between two elongated conducting members of the forceps;
    the output receptacle configured to receive a complementary tool plug of the forceps;
    the input plug configured for mating with a generator receptacle, the input plug configured to receive the heating current from the generator; and
    the actuating component having a hard electrical switch and a lever arm, the lever arm having a first end and a second end, the first end of the lever arm adjacent to the generator portion of the actuator assembly, the second end of the lever arm extending towards a heating end of the forceps, a portion of the lever arm between the first end and the second end configured to engage the hard electrical switch upon displacement of the lever arm in a direction toward the longitudinal axis, and the actuating component being configured to communicate with the generator to selectively actuate the heating current to flow from the input plug to the output receptacle upon engagement of the hard electrical switch by the lever arm;
    the hard electrical switch connecting the actuator assembly to the generator; and
    a jumper cord connecting the tool portion of the actuator assembly to the generator portion of the actuator assembly, the jumper cord separating and providing conduction between the input plug and the output receptacle.

2. The system of claim 1, wherein: the actuating component is configured to communicate with the generator to selectively actuate the heating current to flow with at least two of the following modes of operation of the surgical tool: cutting, coagulation, or an off mode.

3. The system of claim 1, wherein: the input plug and the complementary tool plug each comprise prongs and where the output receptacle and the generator receptacle each comprise at least two sockets complementary to the prongs.

4. The system of claim 1, wherein: the hard electrical switch for actuating the heating current is configured as one of a push button, a slide switch, a toggle switch, a rotating shaft, a joystick, an electrostatic sensor, a piezoelectric sensor, a temperature switch, a rocker switch, a momentary switch, or a voice-activated switch.

5. The system of claim 1,
    wherein the lever switch mechanism is configured to selectively actuate the heating current in response to the displacement of the lever arm by one of the following means: mechanical actuation, electrical resistance, piezoelectric pressure, or electrostatic sensing.

6. The system of claim 1, further comprising:
    the hard electrical switch configured to directly conduct the heating current from the input plug to the output receptacle upon the engagement of the hard electrical switch by the lever arm.

7. The system of claim 1, further comprising:
    a microphone and a voice activation circuitry both included in the actuating component for selectively actuating the heating current.

8. The system of claim 1, wherein: the lever arm is hingedly moveable to engage the hard electrical switch for selectively actuating the heating current.

9. A system for selectively actuating a heating current conductible from a generator to forceps, comprising:
    two elongated conducting members extending from a base end of the forceps to a heating end of the forceps, a longitudinal axis extending from the base end to the heating end between the two elongated conducting members, the base end configured to receive the heating current from the generator through a power cord, the heating end for effectuating at least one of the following modes of operation of the forceps: cutting or coagulation;
    an actuator assembly having a tool portion comprising an output receptacle and a generator portion comprising both an input plug and an actuating component, the tool portion coupled to the generator portion by a jumper cord, the actuator assembly in operable electrical connection with the power cord and the two elongated conducting members, the actuator assembly configured within a base portion of the forceps nearer the base end;

an actuating component of the actuator assembly, the actuating component having a hard electrical switch and a lever arm, the lever arm having a first end and a second end, the first end of the lever arm adjacent to the generator portion of the actuator assembly, the second end of the lever arm extending towards the heating end of the forceps, a portion of the lever arm between the first end and the second end configured to engage the hard electrical switch upon displacement of the lever arm in a direction toward the longitudinal axis of the forceps, and the actuating component being configured to communicate with the generator to selectively actuate the heating current to flow from the generator to the heating end of the forceps upon engagement of the hard electrical switch by the lever arm; and the hard electrical switch connecting the actuator assembly to the generator.

10. The system of claim 9, wherein: the lever arm is configured for human operation by a hand or an upper body.

11. The system of claim 9, wherein: the hard electrical switch for actuating the heating current is configured as one of a push button, a slide switch, a rotating shaft, a joystick, an electrostatic sensor, a piezoelectric sensor, a temperature switch, a rocker switch, a momentary switch, or a voice-activated switch.

12. The system of claim 9, wherein the lever switch mechanism is configured to selectively actuate the heating current in response to a displacement of the lever arm by one of the following means: mechanical actuation, electrical resistance, piezoelectric pressure, or electrostatic sensing.

13. The system of claim 9, wherein: the actuator assembly is configured for one of the following external mountings: being held by a human hand, mounted to an operating table, mounted to a positioning arm, mounted actuatably to a human upper body, or mounted to another piece of operating room equipment.

14. The system of claim 9, further comprising:

the hard electrical switch configured to directly conduct the heating current from the generator to the two elongated conducting members upon the engagement of the hard electrical switch by the lever arm.

15. The system of claim 9, further comprising:

an input plug connected to the generator and a blade connector, the input plug for mating with the power cord conductive to the generator, the blade connector for mating with the two elongated conducting members.

16. The system of claim 9, wherein: the actuating component of the actuator assembly is integral with the two elongated conducting members.

17. The system of claim 9, wherein: the lever arm is hingedly moveable to engage the hard electrical switch for selectively actuating the heating current.

* * * * *